United States Patent
Petersen

(10) Patent No.: US 8,608,882 B2
(45) Date of Patent: Dec. 17, 2013

(54) COMPOSITE WEB, DISPOSABLE DIAPER AND PROCESS FOR MANUFACTURING THEREOF

(75) Inventor: Johann F. Petersen, Grevenbroich (DE)

(73) Assignee: 3M Innovative Properties Company, St. Paul, MN (US)

( * ) Notice: Subject to any disclaimer, the term of this patent is extended or adjusted under 35 U.S.C. 154(b) by 986 days.

(21) Appl. No.: 11/916,939

(22) PCT Filed: Jun. 8, 2006

(86) PCT No.: PCT/EP2006/005488
§ 371 (c)(1),
(2), (4) Date: Jul. 2, 2008

(87) PCT Pub. No.: WO2006/131364
PCT Pub. Date: Dec. 14, 2006

(65) Prior Publication Data
US 2008/0281286 A1    Nov. 13, 2008

(30) Foreign Application Priority Data

Jun. 9, 2005  (EP) ..................................... 05012431
Jun. 9, 2005  (EP) ..................................... 06009347

(51) Int. Cl.
*E06B 9/26*     (2006.01)
*A61F 13/15*    (2006.01)

(52) U.S. Cl.
USPC ........................................ 156/65; 604/385.01

(58) Field of Classification Search
USPC .......... 604/385.24, 385.27, 289, 290; 156/60, 156/73.1
See application file for complete search history.

(56) References Cited

U.S. PATENT DOCUMENTS

| 4,001,366 A | 1/1977 | Brumlik |
| 4,067,337 A | 1/1978 | Ness |
| 4,376,440 A | 3/1983 | Whitehead et al. |
| 4,381,781 A | 5/1983 | Sciaraffa et al. |
| 4,475,913 A | 10/1984 | Hlaban |
| 5,300,058 A | 4/1994 | Goulait et al. |
| 5,399,219 A | 3/1995 | Roessler et al. |
| 5,468,428 A | 11/1995 | Hanschen et al. |
| 5,487,809 A | 1/1996 | Goulait et al. |
| 5,611,790 A | 3/1997 | Osborn et al. |
| 5,676,652 A | 10/1997 | Hunter et al. |
| 5,705,013 A | 1/1998 | Nease et al. |
| 5,759,317 A | 6/1998 | Justmann |

(Continued)

FOREIGN PATENT DOCUMENTS

| EP | 0 521 883 | 8/1996 |
| EP | 1 142 547 | 10/2001 |

(Continued)

OTHER PUBLICATIONS

PCT International Search Report, PCT/EP2006/005488, dated Sep. 1, 2006.

*Primary Examiner* — Melanie Hand

(57) ABSTRACT

The present invention relates to a process for manufacturing a composite web for use in a disposable product, the process comprising the steps of: a) providing a continuous web of material; b) creating in the web a longitudinally repeating pattern of windows; and c) attaching at least one strip to the web, said strip at least partially covering the windows and having different functional characteristics than the web. The present invention also relates to a composite web formed in accordance with this process and to panels obtainable by cutting said web in cross direction.

22 Claims, 6 Drawing Sheets

(56) References Cited

U.S. PATENT DOCUMENTS

| | | |
|---|---|---|
| 5,904,673 A | 5/1999 | Roe et al. |
| 5,906,604 A | 5/1999 | Ronnberg et al. |
| 6,017,406 A * | 1/2000 | Vogt .............................. 156/73.1 |
| 6,039,717 A | 3/2000 | Larsson |
| 6,051,094 A | 4/2000 | Melbye et al. |
| 6,086,571 A | 7/2000 | Guevara et al. |
| 6,241,716 B1 | 6/2001 | Ronnberg |
| 6,334,858 B1 | 1/2002 | Ronnberg et al. |
| 6,406,468 B1 | 6/2002 | Dilnik et al. |
| 6,428,526 B1 | 8/2002 | Heindel et al. |
| 6,432,099 B2 | 8/2002 | Ronnberg |
| 6,500,163 B2 | 12/2002 | Ronnberg et al. |
| 6,524,294 B1 | 2/2003 | Hilston et al. |
| 6,531,207 B1 | 3/2003 | Eaton et al. |
| 6,669,678 B2 | 12/2003 | Hermansson et al. |
| 6,692,476 B1 | 2/2004 | Minato et al. |
| 6,702,917 B1 | 3/2004 | Venturino et al. |
| 7,329,245 B2 | 2/2008 | Torigoshi et al. |
| 7,407,496 B2 | 8/2008 | Petersen |
| 7,658,813 B2 | 2/2010 | Petersen |
| 2002/0016581 A1 | 2/2002 | Kline et al. |
| 2002/0151858 A1 | 10/2002 | Karami et al. |
| 2003/0097110 A1* | 5/2003 | Erdman ..................... 604/385.3 |
| 2004/0147890 A1* | 7/2004 | Nakahata et al. ........ 604/385.01 |
| 2006/0282053 A1 | 12/2006 | Rohrl |
| 2007/0039142 A1 | 2/2007 | Petersen et al. |

FOREIGN PATENT DOCUMENTS

| | | | |
|---|---|---|---|
| EP | 1 066 008 | 3/2004 | |
| EP | 1066008 B1 * | 3/2004 | .............. A61F 13/58 |
| JP | 11-181374 | 7/1999 | |
| JP | 2002-45214 | 2/2002 | |
| JP | 2003-102777 | 4/2003 | |
| WO | WO 97/36566 | 10/1997 | |
| WO | WO 03/002053 | 1/2003 | |
| WO | WO 03/003962 | 1/2003 | |
| WO | WO 2004/105668 | 12/2004 | |

* cited by examiner

COMPOSITE WEB, DISPOSABLE DIAPER AND PROCESS FOR MANUFACTURING THEREOF

Cross Reference to Related Applications

This application is a national stage filing under 65 U.S.C. 371 of PCT/EP2006/005488, filed Jun. 8, 2006, which claims priority to European Application No. 06009347.3, filed Jun. 9, 2005, and European Application No. 05012431.2, filed Jun. 9, 2005, the disclosures of which are incorporated herein by reference in there entirety.

TECHNICAL FIELD

The present invention relates to a process for manufacturing a composite web for use in disposable products, particularly disposable diapers such as adult incontinence articles, a composite web for a disposable product, a process for manufacturing disposable diapers, and a disposable diaper. The disposable product may particularly be a diaper, and adult incontinence article, and the like.

BACKGROUND ART

WO 03/002053 relates to a sanitary absorbent article including a hook-and-loop-type fastener for releasably attaching a first and a second part of the article to each other. The first part is overlapping the second part when the parts are attached to each other. The fastener includes a hook member affixed to the first part of the article and a loop member affixed to the second part of the article, wherein each member comprises a base portion having a bottom surface affixed to the first or second part of the article and an opposite top surface containing hook elements and loop elements, respectively. The fastener has a first end region distal to the overlapping edge of the first part, in which the engagement force between the hooks and loops element of the members is reduced. This type of sanitary absorbent articles is also known as belt-type diapers or belted diapers.

Further belt-type diapers are disclosed in EP-A-1 142 547, US-A-2002/0151858, US-A-2001/0034511, U.S. Pat. Nos. 6,500,163, 6,432,099, 6,334,858, 6,241,716; 6,086,571, 5,906,604 and U.S. Pat. No. 5,904,673.

WO 2004/105668 A1 discloses a single-use hygiene article comprising a chassis with a front region and a rear region wherein at both sides of the rear region side flaps are directly or indirectly attached. Between the front region and the rear region is a crotch region 14.

U.S. Pat. No. 4,381,781 discloses an elasticized waist diaper in which a layer of elastic material is positioned in an opening in the waist area of the diaper. The elastic layer is located such that it forms a portion of the waist edge of the diaper. The elastic layer may be formed from the same piece of elastic material as is used for the diaper leg elastic.

U.S. Pat. No. 6,692,476 B1 discloses a similar arrangement of a disposable diaper including a laminated panel that includes a liquid-pervious topsheet, a liquid-impervious backsheet and a liquid-absorbent core disposed therebetween. Side flaps of the panel are provided with leg-opening elastic members rectilinearly extending longitudinally thereof between the front and rear waist regions and secured under tension to the respective side flaps. The rear waist region of the panel is provided between the respective side edges of the core and the respective leg-opening elastic members with a pair of stretchable regions being elastically stretchable transversely of the panel.

Generally, the production of continuous webs with uniform machine direction and/or cross direction elastic features, or with continuous zoned elastification in cross direction are known in the art of hygiene products and used for the production of diapers.

SUMMARY OF THE INVENTION

It is an object of the present invention to provide an improved process for manufacturing a composite web for use in a disposable product as well as an improved composite web. A further object of the present invention is to provide an improved process for manufacturing disposable diapers as well as to provide an improved disposable diaper. These objects are achieved with the features of the claims.

According to the present invention, a process for manufacturing a composite web for use in a disposable product comprises the steps of providing a continuous web of material, preferably a non-woven, woven, fabric, scrim, film, or paper material, creating in the web a longitudinally repeating pattern of windows, and attaching one or more strips to the web. The strip(s) cover the windows at least partially and have different functional characteristics, particularly different elastic properties, than the web. The strip(s) may be provided as continuous tapes or as individual patches. If the strip(s) are provided as patches, it is preferred that each patch at least partially covers a single window.

The process may comprise the additional step of providing one or more fastening tabs and attaching the fastening tab(s) to sections of the composite web transversally of the strips, i.e. in the cross machine direction (CD direction).

The step of creating a longitudinally repeating pattern of windows may be particularly performed by perforating, scoring, slitting, abrading, melting and/or cutting. This may be accomplished, e.g., by a die cutting process, particularly rotary die cutting. In accordance with a particularly preferred embodiment, the web material within the windows is cut out and removed from the web material.

The repeating pattern of windows in the web may be longitudinally and/or transversally offset. In accordance with a preferred embodiment, the windows are both longitudinally and transversally offset. The windows may have a wide variety of shapes including, for example, rectangular, oval, circular.

The strips are typically provided from a continuous roll of material, preferably an elastic material. Preferably, the strips or patches are provided and fed to the web by one or more vacuum wheel applicators. Advantageously, the strips or patches are attached to the web by adhesive bonding, thermal bonding, or sonic bonding or combinations of common bonding methods along at least two of the edges of the window. The patches may be slightly larger than the windows so that they can be attached along at least two opposing edges of the windows and patches. The strips or patches may also fit into the windows so as to form a butt joint. The elastic material that is preferably used for the patches may be any type of elastic, but is preferably a multi-layer elastic material comprising an elastic core and at least one less elastic or non-elastic skin layer. Such elastic materials are disclosed, e.g., in EP 0 521 883 and EP 1 066 008.

Another aspect of the present invention relates to a composite web for a disposable product, comprising a web having a longitudinally repeating pattern of windows forming designated sections, wherein the windows are at least partially covered with strips, such as patches, having different functional characteristics, preferably different elastic properties, than the web. Typically, the web is a non-woven, woven, fabric, scrim, film or paper material. The composite web may be provided with one or more fastening tabs attached to sections of the composite web transversally of the strips. The windows in the web may be present in the form of perforations, scorings, slits and/or cut-outs. Preferably, at least parts of the web material within the windows is removed. The windows are advantageously created in the web to be both longitudinally and transversally offset. The strips may be attached to the web by adhesive bonding, thermal bonding, or sonic bonding or combinations of common bonding methods.

Where the strips or patches are made from an elastic material, e.g., a multilayer elastic material, the composite web is provided with elasticity in the areas of the windows.

According to a further aspect of the present invention, a process for manufacturing disposable diapers or adult incontinence articles is disclosed. This process relating to a diaper comprises the steps of providing a continuous web of a plurality of diaper chassis, providing a composite web having a longitudinally and optionally transversally repeating pattern of windows which are at least partially covered with strips (e.g., patches) having different characteristics than the web, providing individual front, rear and/or belt panels by cutting said composite web in cross-direction and thereafter intermittently attaching said panels to the web of diaper chassis. The present invention also relates to a diaper comprising a chassis with a front and a rear panel or belt manufactured according to the above-mentioned process.

A specific advantage of the various aspects of the present invention is that the process and composite web may be used with existing diaper manufacturing equipment. The process and composite web according to the present invention may be particularly advantageously used in the manufacturing of diapers or adult incontinence articles which are made from a diaper chassis and front and rear panels or belts which do not have elastic functionality. Typically, in the manufacturing of adult incontinence articles front and rear side panels or belts are supplied from a continuous roll of inelastic material (e.g. non-woven material) that is attached to the chassis so as to extend transversally from both longitudinal edges of the chassis.

Typically, these side panels are about 20 cm to 25 cm wide and 15-30 cm in height. The front panel may not require any elasticity because it is generally only wrapped towards the rear side of the wearer for reasons of comfort. On the contrary, with the composite web and process according to the present invention it is advantageously possible to provide the rear panel with elastic properties so as to allow some degree of stretching, e.g., between 3 and 10 cm per side, in order to increase the fastening and wearing comfort of the incontinence article.

Belt style diapers are typically wider, as they surround the entire body with the left and right belt elements and are attached either at the front on each other or to the front part of the diaper, possibly in specific designated landing zones. A typical length of each belt element is about 50 cm. Such belt systems are typically between 8 and 20 cm high. The process according to this invention will allow the production of elastic strips or patches into a basically non elastic and thus cheaper nonwoven web. It will also enable the elastification of left and right belt portions from one web, followed by separation and placement to the diaper.

By use of the composite web of the invention typical manufacturing equipment and processes can be used because the front and rear panels are made from a single roll of a composite web with different elastic properties along its length. Thus, with the composite material and process according to the invention, it is possible to provide improved elasticated disposable articles without substantial investment in additional manufacturing equipment.

The present invention may generally use an inelastic non-woven web material for the front and rear side panels which can be provided from a single roll of material as is done on existing manufacturing equipment. This web material may be provided with fastening tabs, wherein typically one or two fastening tabs with mechanical or adhesive fastening means are provided at the rear panel and none on the front panel. The areas of the composite web according to the present invention comprising the cut out windows with the superposed strips or patches are arranged to be in the section of the rear panel of the diaper. The windows may have a size of, for example, 4 cm in width and 25 cm in length. The elastic material from which the patches are preferably made provide an effective elastic zone of, e.g., between 3 and 10 cm per side so as to provide elasticity to the rear panels.

The composite web according to the present invention which may be seen as a repeating pattern of longitudinally repeating front and rear panels, may be fed into existing applicators of diaper manufacturing lines. The composite web may be dispensed in a registered way to the diaper chassis. The resulting diaper comprises a diaper chassis, inelastic front panels and elastic rear panels. This can be achieved with essentially the same manufacturing equipment as previously used to manufacture diapers with both non-elastic front and rear panels.

The scope of this invention is described as example, but not meant to be limited to elastic strips or patches in non elastic webs. In general, it is a process to provide differentiated transversal and/or longitudinal functionality of webs and strips. These could include without being complete different color, breathability, haptic properties, softness, transparency, decorative features.

BRIEF DESCRIPTION OF THE DRAWINGS

In the following, preferred embodiments of the present invention will be described with reference to the drawings in which.

DETAILED DESCRIPTION OF PREFERRED EMBODIMENTS

Figure 1:
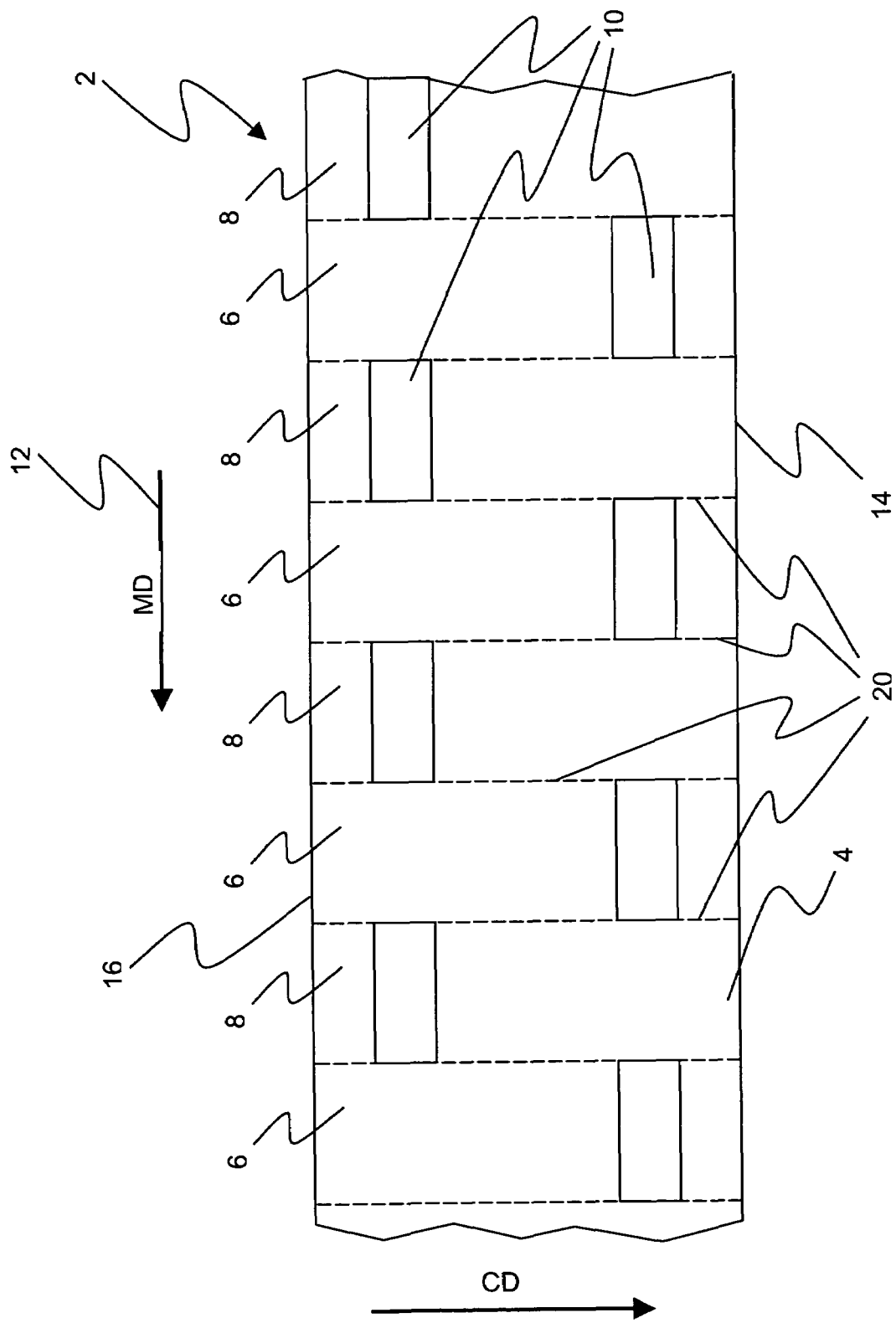
FIG. 1 is a schematic view of a web material that can be used for the manufacture of a composite web for belt style diapers according to the present invention.

A composite web 2 according to the present invention comprises a web 4 of material, preferably a non-woven web material which has a repeating pattern of sections 6, 8 with windows 10 in the longitudinal direction 12, i.e. machine direction (MD). Preferably, the windows 10 are both longitudinally and transversally offset so that in each section 6 a window 10 is provided closer to a first longitudinal edge 14 and in each adjacent section 8 the windows 10 are provided closer to the opposite longitudinal edge 16. Accordingly, in the embodiment shown in FIG. 1 the windows 10 are arranged in a longitudinally and transversally offset configuration.

Figure 2:
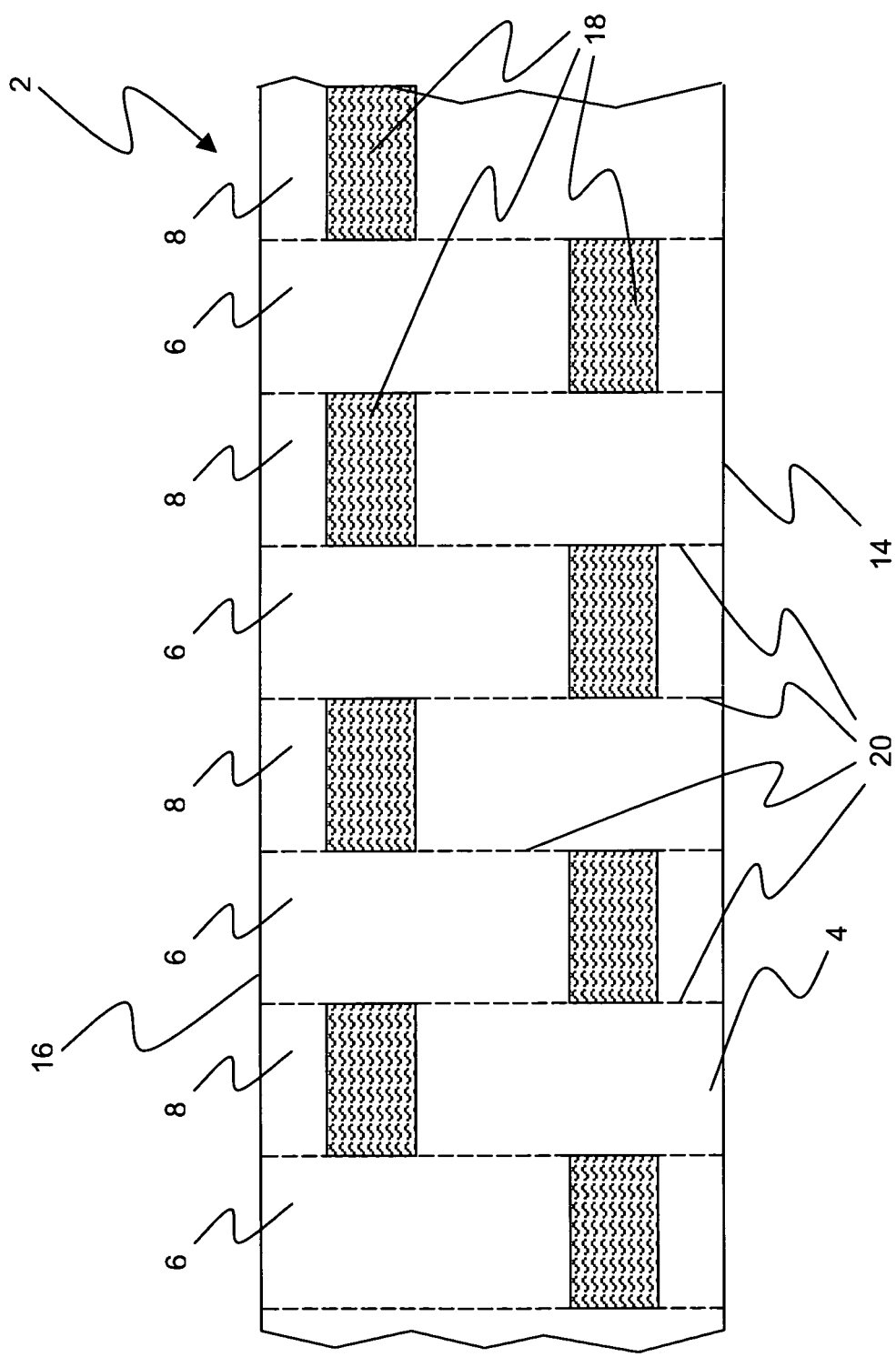
FIG. 2 is a schematic view of a composite web for belt style diapers comprising patches on the windows of the web shown in FIG. 1.

Referring to FIG. 2, the web 4 is shown similarly as in FIG. 1, however, with strips in the form of individual patches 18 covering the windows 10. The patches 18 which impart different functional characteristics to the composite web 2 in the areas of the windows 10 are preferably made from an elastic material. As can be seen upon a comparison of FIGS. 1 and 2, the patches 18 are generally slightly larger than the windows 10 so that the patches 18 can be attached to the web 4 generally around the edges of the windows 10. The attachment can be accomplished, for example, by means of adhesive bonding, thermal bonding and/or sonic bonding.

The composite web 2 shown in FIG. 2 can be used, for example, as belt or rear side panels of disposable diapers, particularly adult incontinence articles. To this end, the composite web is cut along schematically illustrated cut lines 20 separating sections 6 and 8 from one another. After cutting of the sections 6 and 8, the section 6 may be used as a right belt or rear side panel of the diaper and section 8 may be used as a left belt or rear side panel of the diaper or vice versa.

Accordingly, with the composite web 2 according to the present invention left and right belt elements or side rear panels can be cut from a single roll of continuous web material without the need of supplying two separate materials for the respective belt elements or side panels.

Figure 3A:
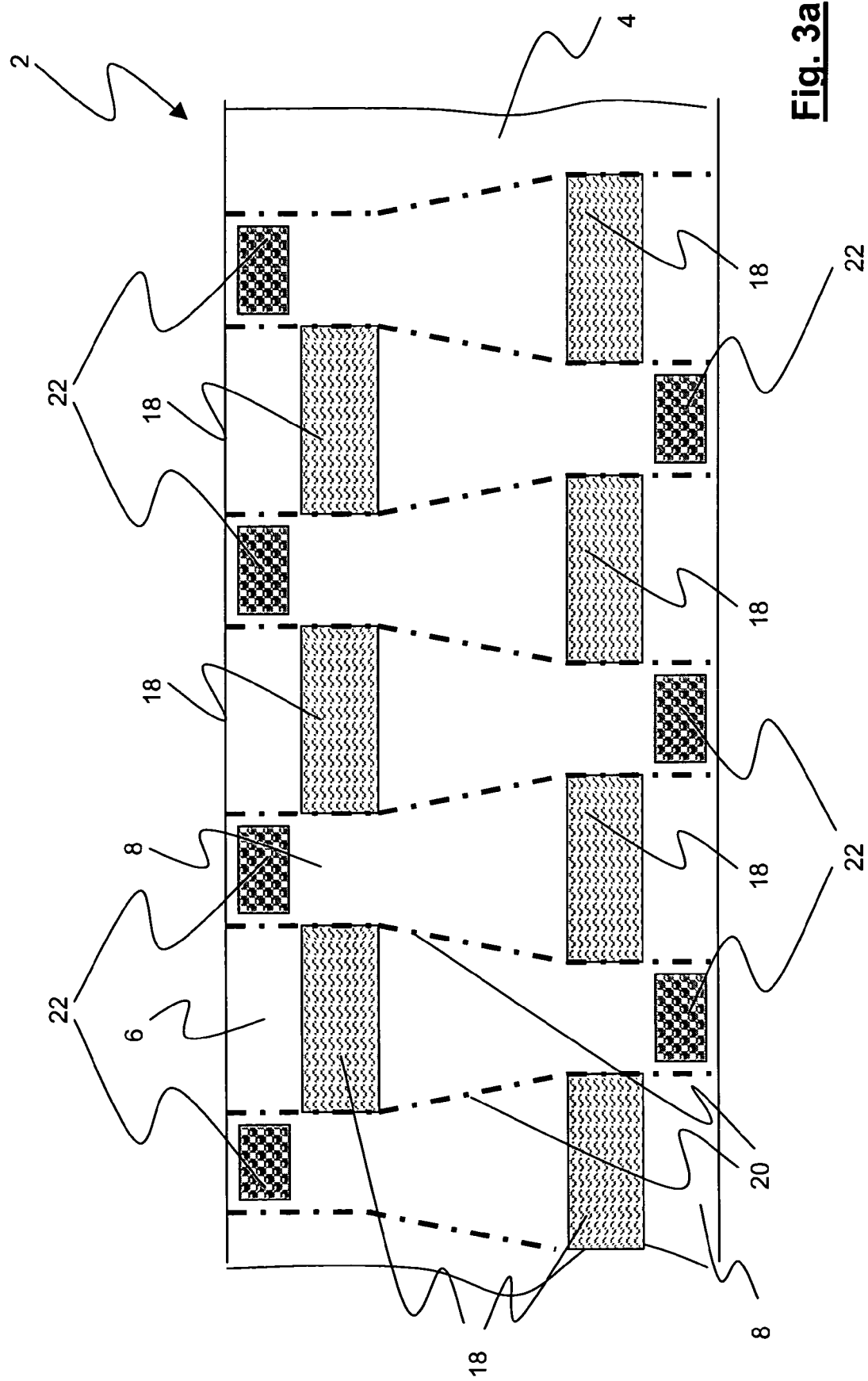
FIG. 3a is a schematic illustration of another embodiment of a composite web for belt style diapers according to the present invention in which cut lines for side panel members for disposable diapers are shown.

Another embodiment of the composite web 2 according to the present invention is shown in FIG. 3a. According to this embodiment, the composite web 2 comprises a web material 4 and first and second sections 6, 8. In accordance with this embodiment, the sections 6, 8 are provided in a form of a bottle neck instead of rectangles as shown in connection with the embodiment of FIGS. 1 and 2. The windows 10 in the web 4 according to the embodiment shown in FIG. 3a are also covered with patches 18. The windows 10 and patches 18 are also arranged in a longitudinally and transversally offset configuration. Furthermore, each of the sections 6, 8 is provided with a fastening tab 22, preferably a mechanical fastener element like a hook tape. The cut lines 20 illustrated in FIG. 3a are inclined with respect to the cross machine direction (CD), wherein longitudinally adjacent cut lines 20 are alternately inclined so as to define the trapezoidal shape of the sections 6, 8.

Similarly as with the embodiment of FIG. 2, the composite web 2 according to the embodiment of FIG. 3a can be cut along the cut lines 20 so as to form respective left and right belt elements or rear side panels that can be attached to diapers, like adult incontinence articles.

Figure 3B:
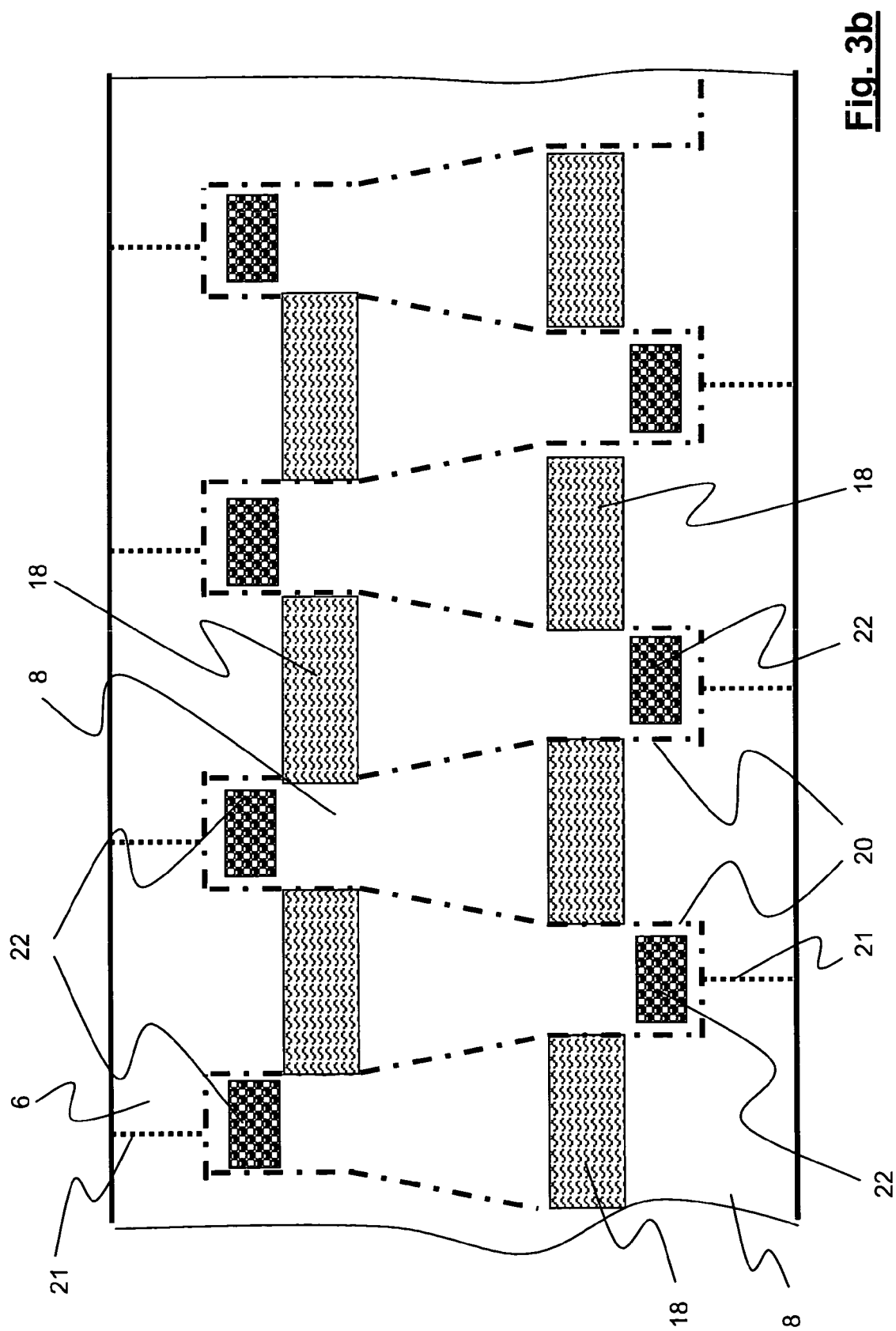
FIG. 3b is a schematic illustration of another embodiment of a composite web for belt style diapers according to the present invention in which other cut lines for side panel members for disposable diapers are shown.

In the embodiment shown in FIG. 3b, the composite web 2 generally corresponds to the web of FIG. 3a. However, the cut lines are different in this embodiment. The sections 6, 8 of the composite web 2 are provided with cut lines 20 (dot-dash lines) in a center region of the web, and with additional cut lines 21 (dotted lines) at the edge regions of the web. Advantageously, these cut lines can be provided sequentially, wherein it is preferred that the cut lines 20 in the center region are provided before the cut lines 21 in the edge regions are made.

Figure 4:
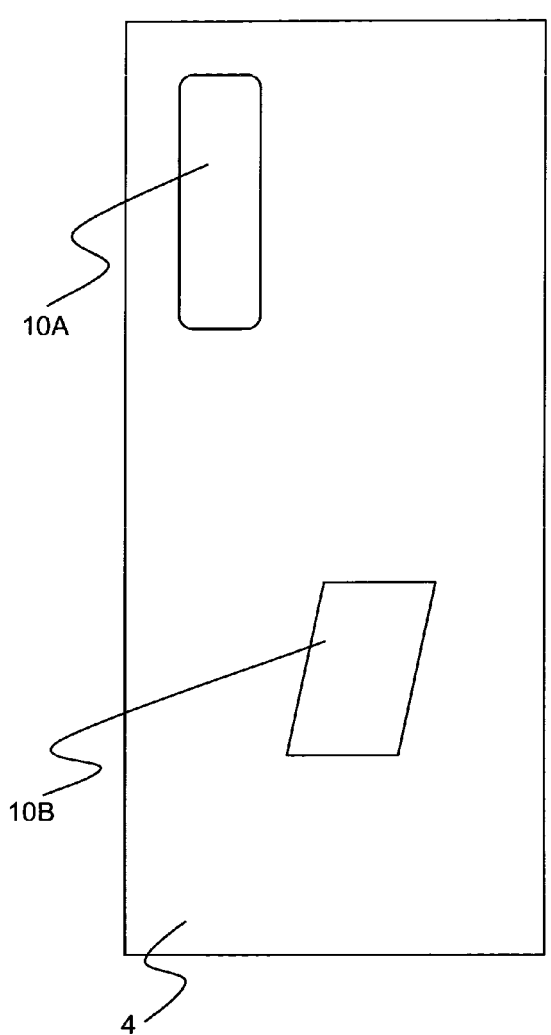
FIG. 4 illustrates various shapes of windows that can be used in the composite web according to the present invention.
Figure 5:
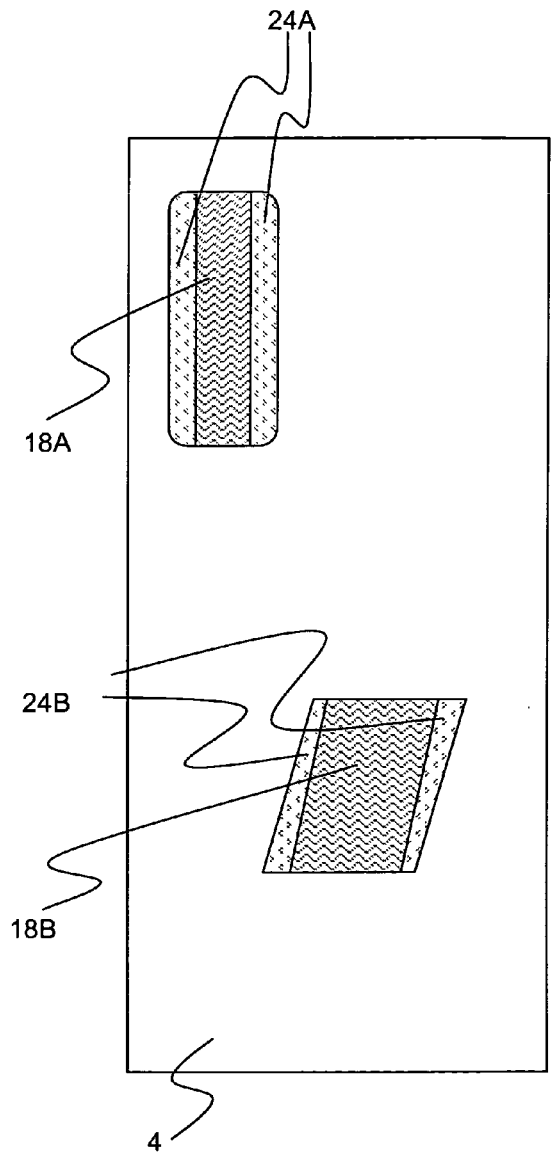
FIG. 5 shows the windows of FIG. 4 covered with patches.

In FIG. 4, various types of window shapes are schematically illustrated that can be used in the composite web 2 according to the present invention. For example, the window 10A in FIG. 4 is generally rectangular, while window 10B is generally parallelogram-shaped. FIG. 5 illustrates patches 18 attached to the windows 10 shown in FIG. 4. As can be seen in FIG. 5, the patches 18 are generally somewhat larger than the windows 10 in order to provide for some additional area 24 that can be used to attach the patches 18 to the web 4. For example, in the case of a rectangular window 10A, the patch 18A may be somewhat wider than the window 10A so as to provide two longitudinal strips 24A for attachment of the patch 18A to the web 4. Similarly, in the case of the parallelogram-shaped window 10B, the patch 18B is also parallelogram-shaped and somewhat wider than the window so as to provide attachment strips 24B on both sides of the window which can be used to attach the patch 18B to the web. It is also possible to attach the patches 18 completely around the windows 10 so as to provide an attachment region completely around the window.

Figure 6:
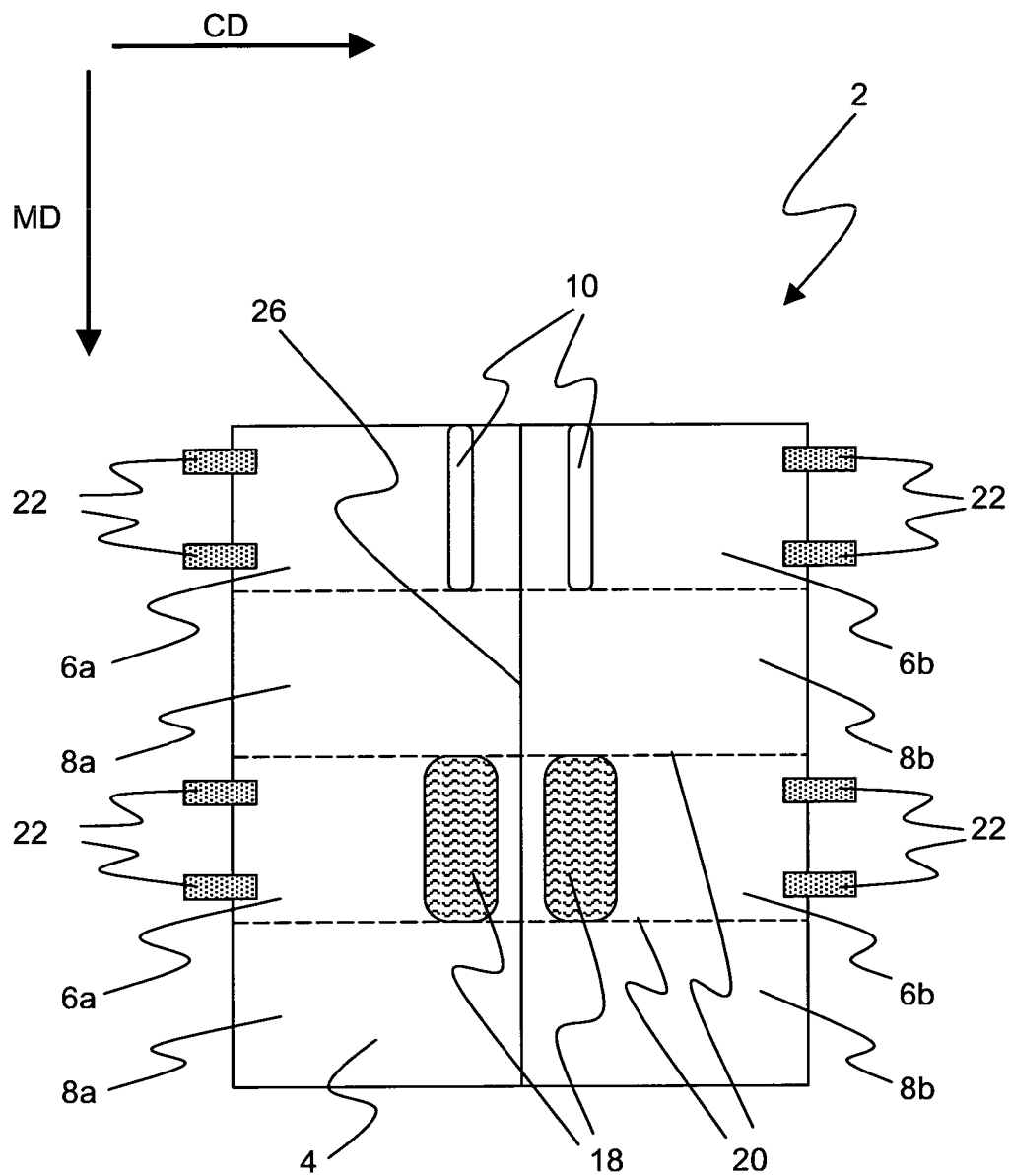
FIG. 6 shows another embodiment of the composite web for side panel style diapers according to the present invention during its manufacturing process.

In FIG. 6 a further embodiment of a composite web 2 according to the present invention is illustrated. The composite web 2 comprises a web 4, e.g., a non-woven web. Similarly as with the previous embodiments, the composite web 2 comprises in the longitudinal direction 12, i.e. the machine direction (MD), various alternating sections 6, 8 that may be separated along cross machine direction (CD) cut lines 20. Furthermore, in accordance with this embodiment of the composite web 2, a longitudinal or machine direction cut line 26 is provided that separates the various sections 6, 8 into left and right sections 6a, 8a, 6b, 8b. The windows 10 provided in sections 6a, 6b are covered with patches 18 in order to provide regions of different functional characteristics in the composite web 2. Moreover, the sections 6a, 6b may be provided the with fastening tabs 22.

Accordingly, with the composite web of the present invention presently used diaper manufacturing equipment can be used to provide improved diapers based on the composite web according to the present invention.

The web material used for the composite web can also be a multilayer web, wherein in each of the layers windows are provided. The strip(s) or patches of material with different functional characteristics can in this case be incorporated between the layers of the web.

The invention claimed is:

1. A process for manufacturing a composite web for use in a disposable product, the process comprising:
    providing a continuous web of material having successive, full-width sections in the longitudinal direction;
    creating in the web a longitudinally repeating pattern of windows, with only one window in each of the full-width, successive sections, wherein the windows created in the web have closed perimeters and are both longitudinally and transversally offset such that in each successive section, the only one window is closer to alternating longitudinal edges of the continuous web of material; and
    attaching at least one strip to the web, said strip at least partially covering the windows and having different functional characteristics than the web.

2. The process of claim 1, wherein the web is a non-woven, woven, fabric, scrim, film, or paper material.

3. The process of claim 1, wherein creating comprises at least one of perforating, scoring, slitting or cutting.

4. The process of claim 1, wherein the web material within the windows is at least partially removed.

5. The process of claim 1, wherein the strip having different functional characteristics is provided from a continuous roll of material.

6. The process of claim 1, wherein the strip is cut into individual patches and fed to the web by one or more vacuum wheel applicators or vacuum feeders, wherein each patch at least partially covers a single window.

7. The process of claim 1, wherein the strip is made from an elastic material.

8. The process of claim 1, wherein the windows are provided in the form of a rectangle, oval, circle, or parallelogram.

9. A composite web for a disposable product, comprising a web having a longitudinally repeating pattern of windows forming designated sections, wherein the windows in the web have closed perimeters and are both longitudinally and transversally offset, wherein said windows are at least partially covered with two or more at least transversally offset strips having different functional characteristics than the web, and wherein each strip at least partially covers at least one but less than all of the windows.

10. The composite web of claim 9, wherein the web is a non-woven, woven, fabric, scrim, film, or paper material.

11. The composite web of claim 9, wherein the windows in the web comprise at least one of perforations, scorings, slits or cutouts.

12. The composite web of claim 9, wherein the web material within the windows is at least partially removed.

13. The composite web of claim 9, wherein the strip having different functional characteristics is made from an elastic material.

14. The composite web of claims 9, wherein the windows are provided in the form of a rectangle, oval, circle or parallelogram.

15. The composite web of claim 9 wound into a roll.

16. A process for manufacturing disposable diapers, the process comprising:
   providing a continuous web of a plurality of diaper chassis;
   providing a composite web comprising a web having a longitudinally repeating pattern of windows forming designated sections, wherein said windows have closed perimeters and are at least partially covered with at least one strip having different functional characteristics than the web, and wherein said windows in the web are both longitudinally and transversally offset;
   providing at least one of individual front, rear or belt panels by cutting said composite web in a cross-direction; and thereafter
   intermittently attaching said panels to the web of diaper chassis.

17. The process of claim 16, wherein the web having a longitudinally repeating pattern of windows is a non-woven, woven, fabric, scrim, film, or paper material.

18. The process of claim 16, wherein the web material within the windows is at least partially removed.

19. The process of claim 16, wherein the at least one strip having different functional characteristics is made from an elastic material.

20. The process of claim 16, wherein the windows are provided in the form of a rectangle, oval, circle or parallelogram.

21. A disposable diaper comprising a chassis with at least one of a front, a rear panel, or a belt manufactured according to the process of claim 16.

22. The composite web of claim 16, wherein each strip is a patch that at least partially covers a single window.

\* \* \* \* \*